(12) United States Patent
Boutell

(10) Patent No.: US 9,702,002 B2
(45) Date of Patent: *Jul. 11, 2017

(54) NUCLEIC ACID SAMPLE ENRICHMENT FOR SEQUENCING APPLICATIONS

(71) Applicant: Illumina Cambridge Limited, Essex (GB)

(72) Inventor: Jonathan Mark Boutell, Essex (GB)

(73) Assignee: ILLUMINA, INC., San Diego, CA (US)

( * ) Notice: Subject to any disclaimer, the term of this patent is extended or adjusted under 35 U.S.C. 154(b) by 205 days.

This patent is subject to a terminal disclaimer.

(21) Appl. No.: 14/243,661

(22) Filed: Apr. 2, 2014

(65) Prior Publication Data

US 2014/0274743 A1    Sep. 18, 2014

Related U.S. Application Data

(63) Continuation of application No. 13/119,131, filed as application No. PCT/GB2009/002366 on Oct. 2, 2009, now Pat. No. 8,728,764.

(60) Provisional application No. 61/102,232, filed on Oct. 2, 2008.

(51) Int. Cl.
C12Q 1/68 (2006.01)

(52) U.S. Cl.
CPC ........... *C12Q 1/6874* (2013.01); *C12Q 1/686* (2013.01); *C12Q 1/6806* (2013.01)

(58) Field of Classification Search
CPC ........ C12Q 2525/161; C12Q 2531/113; C12Q 2565/501; C12Q 1/6806; C12Q 1/686; C12Q 1/6874
USPC ...................................... 435/91.2
See application file for complete search history.

(56) References Cited

U.S. PATENT DOCUMENTS

| | | | |
|---|---|---|---|
| 5,302,509 A | 4/1994 | Cheeseman | |
| 5,326,692 A | 7/1994 | Brinkley et al. | |
| 5,405,746 A | 4/1995 | Uhlen | |
| 5,432,065 A | 7/1995 | Fuller | |
| 5,474,796 A | 12/1995 | Brennan | |
| 5,508,169 A | 4/1996 | Deugau et al. | |
| 5,514,539 A | 5/1996 | Bukh et al. | |
| 5,547,839 A | 8/1996 | Dower et al. | |
| 5,589,332 A | 12/1996 | Shih et al. | |
| 5,616,478 A | 4/1997 | Chetverin | |
| 5,629,158 A | 5/1997 | Uhlen | |
| 5,641,658 A | 6/1997 | Adams et al. | |
| 5,645,801 A | 7/1997 | Bouma et al. | |
| 5,645,994 A | 7/1997 | Huang | |
| 5,683,872 A | 11/1997 | Rudert et al. | |
| 5,690,894 A | 11/1997 | Pinkel et al. | |
| 5,753,439 A | 5/1998 | Smith et al. | |
| 5,795,714 A | 8/1998 | Cantor et al. | |
| 5,800,992 A | 9/1998 | Fodor et al. | |
| 5,830,663 A | 11/1998 | Embleton et al. | |
| 5,837,466 A | 11/1998 | Lane et al. | |
| 5,843,660 A | 12/1998 | Schumm et al. | |
| 5,922,574 A | 7/1999 | Minter | |
| 5,928,875 A | 7/1999 | Breen et al. | |
| 5,939,291 A | 8/1999 | Loewy et al. | |
| 5,976,802 A | 11/1999 | Ansorge et al. | |
| 6,060,288 A | 5/2000 | Adams et al. | |
| 6,090,592 A | 7/2000 | Adams et al. | |
| 6,107,023 A | 8/2000 | Reyes et al. | |
| 6,280,949 B1 | 8/2001 | Lizardi | |
| 6,300,070 B1 | 10/2001 | Boles et al. | |
| 6,316,229 B1 | 11/2001 | Lizardi et al. | |
| 6,322,971 B1 | 11/2001 | Chetverin et al. | |
| 6,326,489 B1 | 12/2001 | Church et al. | |
| 6,406,893 B1 | 6/2002 | Knapp et al. | |
| 6,432,680 B1 | 8/2002 | Lin et al. | |
| 6,468,751 B1 | 10/2002 | Adams et al. | |
| 6,489,103 B1 | 12/2002 | Griffiths et al. | |
| 6,511,803 B1 | 1/2003 | Church et al. | |
| 7,754,429 B2 | 7/2010 | Rigatti et al. | |
| 8,728,764 B2 * | 5/2014 | Boutell ................ | C12Q 1/6806 435/91.2 |
| 8,999,642 B2 * | 4/2015 | Sabot .................... | C12Q 1/6806 435/6.11 |
| 2003/0148284 A1 | 8/2003 | Vision et al. | |
| 2005/0100900 A1 | 5/2005 | Kawashima et al. | |
| 2007/0269817 A1 | 11/2007 | Shapero | |
| 2009/0156412 A1 * | 6/2009 | Boyce, IV ......... | C12N 15/1006 506/3 |

FOREIGN PATENT DOCUMENTS

| | | |
|---|---|---|
| DE | 4141178 | 6/1993 |
| DE | 19515552 | 10/1996 |
| EP | 0 224 126 | 6/1987 |
| EP | 0 356 021 | 2/1990 |
| EP | 0 374 665 | 6/1990 |
| EP | 0487104 | 5/1992 |
| EP | 0543484 | 5/1993 |

(Continued)

OTHER PUBLICATIONS

Shendure, et al., "Next-generation DNA sequencing", Nature Biotechnology 26(10), 2008, 1135-1145.
Wikipedia, "The definition of "enzyme" from Wikipedia, the free encyclopedia", Printed on May 19, 2011.
Abel, , "Fiber-Optic Evanescent Wave Biosensor for the Detection of Oligonucleotides", Analytical Chemistry, vol. 68, Sep. 1996, 2905-2912.
Babic et al., "MutS interaction with mismatch and alkylated base containing DNA molecules detected by optical biosensor", Mutation Research 372:87-96, 1996.
Beattie, et al., "Hybridization of DNA targets to glass-tethered oligonucleotide probes", Molecular Biotechnology, 4, 1995, 213-225.

(Continued)

*Primary Examiner* — Cynthia B Wilder
(74) *Attorney, Agent, or Firm* — Yan Leychkis; Illumina, Inc.

(57) ABSTRACT

The present invention relates to the field of molecular biology, and more specifically to methods for reducing the complexity of a nucleic acid sample.

17 Claims, 4 Drawing Sheets

(56) References Cited

FOREIGN PATENT DOCUMENTS

| | | |
|---|---|---|
| EP | 0 665 293 | 8/1995 |
| EP | 0701001 | 3/1996 |
| EP | 0 763 135 | 3/1997 |
| EP | 1 019 496 | 7/2000 |
| EP | 1 482 036 | 12/2004 |
| EP | 1117827 | 11/2005 |
| GB | 2233654 | 1/1991 |
| WO | WO 87/06270 | 10/1987 |
| WO | WO 88/10315 | 12/1988 |
| WO | WO 89/01050 | 2/1989 |
| WO | WO 89/09282 | 10/1989 |
| WO | WO 90/02205 | 3/1990 |
| WO | WO 90/06042 | 6/1990 |
| WO | WO 90/09455 | 8/1990 |
| WO | WO 90/11369 | 10/1990 |
| WO | 9106678 | 5/1991 |
| WO | WO 92/04469 | 3/1992 |
| WO | WO 92/10587 | 6/1992 |
| WO | 93/03151 | 2/1993 |
| WO | WO 93/04199 | 3/1993 |
| WO | WO 93/09250 | 5/1993 |
| WO | WO 93/21340 | 10/1993 |
| WO | WO 94/02634 | 2/1994 |
| WO | WO 94/05414 | 3/1994 |
| WO | WO 94/24312 | 10/1994 |
| WO | WO 95/12416 | 5/1995 |
| WO | WO 95/33073 | 12/1995 |
| WO | WO 96/04404 | 2/1996 |
| WO | WO 96/24688 | 8/1996 |
| WO | WO 96/27025 | 9/1996 |
| WO | WO 96/32504 | 10/1996 |
| WO | WO 96/34114 | 10/1996 |
| WO | WO 96/36737 | 11/1996 |
| WO | WO 97/19193 | 5/1997 |
| WO | WO 97/41256 | 11/1997 |
| WO | WO 97/45554 | 12/1997 |
| WO | WO 98/36094 | 8/1998 |
| WO | WO 98/44151 | 10/1998 |
| WO | WO 98/44152 | 10/1998 |
| WO | WO 98/45474 | 10/1998 |
| WO | WO 00/41524 | 7/2000 |
| WO | WO 00/75374 | 12/2000 |
| WO | WO 2007/010251 | 1/2007 |
| WO | WO 2007/010252 | 1/2007 |
| WO | WO 2008/041002 | 4/2008 |
| WO | 2009043335 | 1/2009 |

OTHER PUBLICATIONS

Bentley, et al., "Accurate whole human genome sequencing using reversible terminator chemistry", Nature, vol. 456, No. 7218, Nov. 6, 2008, 53-59.

Blanchard, et al., "Oligonucelotide array synthesis using ink jets", Genome Science and Technology 1(3):225, 1996.

Bronk et al., , "Combined imaging and chemical sensing using a single optical imaging fiber.", Anal. Chem. 67:2750-2757, 1995.

Chee, et al., "Accessing genetic information with high-density DNA arrays", Science 274 (5287), 2001, 601.

Chen, et al., "Isolation of Plasmid DNA Rescued From Single Colonies of Agrobacterium Tumefaciens by Means of Rolling Circle Amplification", Plant Molecular Biology Reporter, 21, 411-415,, 2003, 5.

Cheng, et al., "Chip PCR II Investigation of different PCR ampification systems in microfabricated silicon-glass chips", Nucleic Acids Research 24, 1996, 380-385.

Chrisey, et al., "Covalent attachment of synthetic DNA to self-assembled monolayer films", NAR, 24(15), 1996, 3031-3039.

Chu, et al., "Derivitization of unprotected polynucleotides", NAR, 11 (18), 1983, 6514-6529.

Drmanac et al., , "Sequencing by hybridization: towards an automated sequencing of one million m13 clones arrayed on membranes", Electrophoresis 13:566-573, 1992.

Egan, et al., "Structural studies and chemistry of bacterial polysaccharides. Invesigations of Phosphodiester-Linked Capsular Polysaccharides Isolated from Haemophilus influenzae Types a, b, c, and f: NMR Spectroscopic Identification and Chemical Modification of End", Groups and the Nture of Base-Catalyzed Hydrolytic Depolymerization, J. Am. Chem. Soc., 104, 1982, 2898-2910.

Eggleston et al., , "A helicase assay based on the displacement of fluorescent nucleic acid-binding ligands", Nucleic Acids Research 24(7), 1996.

Ferguson, J A. et al., "A Fiber-Optic DNA Biosensor Microarray for the Analysis of Gene Expression", Nature Biotechnol. vol. 14, 1996, 1681-1684.

Fodor, , "Light-Directed, Spatially Addressable Parallel Chemical Synthesis", Science, vol. 251, 1991, 767-773.

Fu, et al., "Sequencing Double-stranded DNA by Strand Displacement", Nucleic Acids Research vol. 25 No. 3, 1997, 677-679.

Ghosh, et al., "Covalent attachment of oligonucleotides to solid supports", NAR, 15 (13), 1987, 5353-5371.

Gilham, , "The synthesis of Celluloses covalently bound nucleotides, polynucleotids, and nucleic acids", Biochemistry, 1968, 2810-2813.

Gingeras, et al., "Hybridization properties of immobilized nucleic acids", NAR, 15, 1987, 5373-5390.

Guo, Zhen et al., "Direct fluorescence analysis of genetic polymorphisms by hybridization with oligonucleotide arrays on glass supports", Nucleic Acids Research, vol. 22(24), 1994, 5456-5465.

Hahn, et al., "Quantitative polymerase chain reaction with enzyme-linked immunosorbent assay detection of selectively digested amplified sample and control DNA", Anal Biochem 229, 1995, 236-248.

Higuchi et al., , "Kinetic PCR analysis: real-time monitoring of DNA amplification reactions", Bio/Technology 11:1026-1030, 1993.

Joos, et al., "Covalent attachment of hybridizable oligonucleotides to glass supports", Analytical Biochemistry, 247, 1997, 96-101.

Kaneoka et al., , "Solid-phase direct DNA sequencing of allele specific polymerase chain reaction amplified HLA-DR genes", Biotechniques 10(1):30, 32, 34, 1991.

Kremsky, et al., "Immobilization of DNA oligonucelotides containing an aldehyde or carboxylic acid group at the 5' terminus", NAR 15 (7), 1987, 2891-2909.

Kulp et al., , "Polymer immobilized enzyme optrodes for the detection of penicillin", Anal. Chem. 59:2849-2853, 1987.

Lambert et al., , "cDNA library construction from small amounts of RNA using paramagnetic beads and PCR", Nucleic Acids Research 21(3):775-6, 1993.

Lamture, et al., "Direct Detection of Nucleic Acid Hybridization on the Surface of a Charge Coupled-Device", Nucleic Acids Research, 22(11), 1994, 2121-2125.

Lizardi, , "Mutation detection and single-molecule counting using isothermal rolling-circle amplification", Nature Genetics, vol. 19, 1998, 225-232.

Lockhart, D J. et al., "Expression monitoring by hybridization to high-density oligonucleotide arrays", Nature Biotechnology, vol. 14 Dec., ISSN 1087-015., 1996, 1675-1680.

Ludecke, et al., "Cloning defined regions of the human genome by microdissection of banded chromosomes and enzymatic amplification", Nature 338, 1989, 348-350.

Lund, et al., "Assessment of methods for covalent binding of nucleic acids to magnetic beads, Dynabeads, and the characteristics of the bound nucleic acids in hybridization reactions", NAR, 16 (22), 1988, 10860-10881.

Manley et al., "DNA-dependent transcription of adenovirus genes in a soluble whole-cell extract", PNAS 77(7):3855-3859, 1980.

Mardis, , "next-generation DNA sequencing methods", Annual Review of Genomics and Human Genetics, Sep. 2008, 387-402.

Maskos, et al., "Oligonucleotide Synthesis and Hybridisations on Glass Supports: A Novel Linker for Oligonucleotide Synthesis and Hybridisation Properties of Oligonucleotides Synthesized in Situ", Nucleic Acids Researc, 20(7), 1992, 1679-1684.

(56) References Cited

OTHER PUBLICATIONS

Maskos et al., "Parallel analysis of oligodeoxyribonucleotide (oligonucleotide) interaction. I. Analysis of factors influencing oligonucleotide duplex formation", Nucleic Acids Research 20(7):1675-1678, 1992.
Munkholm, C. et al., "Polymer modification of fiber optical imaging fibers", Analytical Chemistry vol. 58 No. 7., 1986, 1427-1430.
Notomi, et al., "Loop-mediated isothermal amplification of DNA", Nucleic Acids Research 28, 2000, i-vii.
Ochman, et al., "Genetic applications of an Inverse Polymerase Chain Reaction", Genetics 120, 1988, 621-623.
O'Donnell-Maloney, et al., "The development of microfabricated array for DNA sequencing and analysis", Tibtech, 14, 1996, 401-407.
Oroskar, et al., "Detection of immobilized amplicons by ELISA-like techniques", Clinical Chemistry 42, 1996, 1547-1555.
Pease, et al., "Light-generated oligonucleotide array for rapid DNA sequence analysis", Proc. Natl. Acad. Sci., vol. 91, Issue 11, 1994, 5502-5026.
Peeters, et al., "Comparison of four biofuncitonal reagents for coupling peptides to proteins and the effect of the three moities on the immunogenicity of the conjugates", Journal of Immunological Methods, 120, 1989, 133-143.
Pirrung, et al., "Comparison of Methods for Photochemical Phosphoramidite-Based DNA Synthesis", Journal of Organic Chemistry, 60(20), 1995, 6270-6276.
Piunno et al., , "Fiber-optic DNA sensor for fluorometric nucleic acid determination", Anal. Chem. 67:2635-2643, Aug. 1995.
Rasmussen, et al., "Covalent immobilization of DNA onto polystyrene microwells: The molecules are only bound at th e5' end", Analytical Biochemistry, 198, 1991, 138-142.
Saiki, et al., "Enzymatic amplification of B-globin genomic sequences and restriction site analysis for diagnosis of sicke cell anemia", Science, 230, 1985, 1350-1354.
Saiki et al., "Genetic analysis of amplified DNA with immobilized sequence-specific oligonucleotide probes", PNAS 86:6230-4, 1989.
Saunders, et al., "PCR amplification of DNA microdissected from a single polytene chromosome band: a comparison with conventional microcloning", Nucleic Acids Research 17, 1989, 9027-9037.
Stamm et al., , "Sanchored PCR: PCR with cDNA couples to a solid phase", Nucleic Acids Research 19(6):1350, 1991.
Steigerwald, et al., "Ligation-mediated PCR Improves the sensitivity of methylation analysis by restriction enzymes and detection of specific DNA Strand breaks", Nucleic Acids Research 18, 1990, 1435-1439.
Sterky, et al., "Direct sequencing of bacterial artificial chromosomes [bacS] prokaryotic genomes by biotin capture PCR", Journal of Biotechnology, vol. 60, 1998, 119-129.
Thomas, et al., "Affymetrix: Genes on Chips", Expr. Opino. Ther. Patents, 8, 1998, 503-508.
Triglia, et al., "A procedure for in vitro amplification of DNA segments that lie outside the boundaries of know sequences", Nucleic Acids Research 16, 1988, 8186.
Vanness et al, , "A versatile solid support system for oligodeoxynucleotide probe-based hybridization assays", Nucleic Acids Research 19(12):3345-3350, 1991.
Vos, et al., "AFLP: a new technique for DNA Fingerprinting", NAR vol. 23 No. 21, 1995, 4407-4414.
Walker, , "Empirical Aspects of Strand Displacement Amplification", PCR Methods Appl 3, 1993, 1-6.
Walker, et al., "Isothermal in vitro amplification of DNA by a restriction enzyme/DNA polymerase system", PNAS, 89, 1992, 392-396.
Walker, et al., "Multiplex strand displacement amplification (SDA) and detection of DNA sequences from *Mycobacterium tuberculosis* and other mycobacteria", Nucleic Acids Research 22, 1994, 2670-2677.
Westin, et al., "Anchored multiplex amplification on a microelectric chip array", Nature Biotechnology 18, 2000, 199-204.
Winn-Deen et al., , "Non-radioactive detection of *Mycobacterium tuberculosis* LCR products in a microtiter plate format", Mol. Cell. Probes 7:179-186, 1993.
Wolf, et al., "Rapid hybridization kinetics of DNA attached to submicron latex particles", NAR, 15, 1987, 2911-2926.
Yang, et al., "Covalent Immobilization of oligonucleotides on modified glass/silicon surfaces for solid-phase DNA hybridization and amplification", Chemistry Letters, 1998, 257-8.
Yershov, et al., "DNA analysis and diagnostics on oligonucleotide microchips", PNAS US 93, 1996, 4913-4918.

* cited by examiner

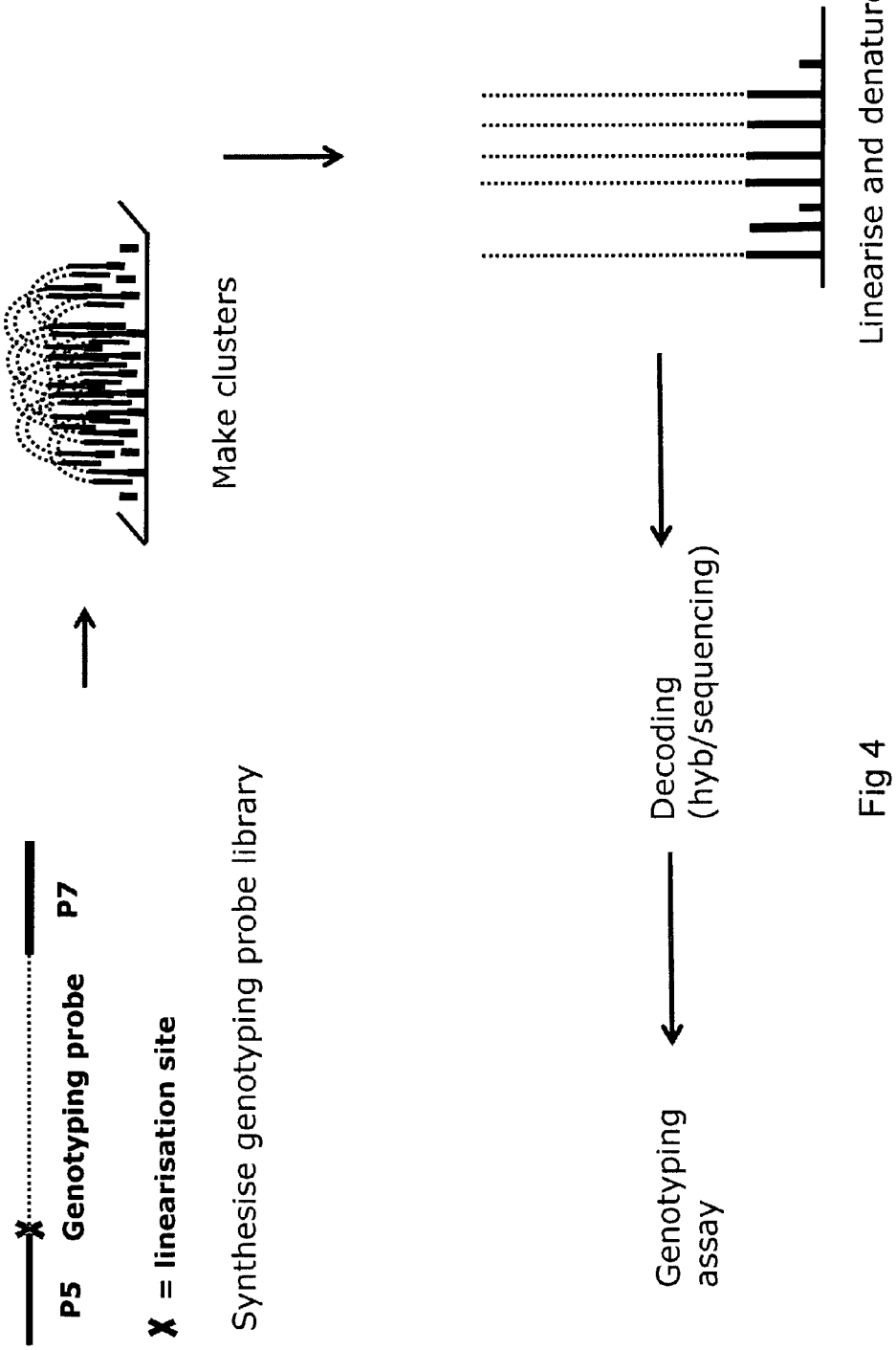

NUCLEIC ACID SAMPLE ENRICHMENT FOR SEQUENCING APPLICATIONS

CROSS REFERENCE TO RELATED APPLICATIONS

This application is a continuation of U.S. application Ser. No. 13/119,131 filed Mar. 15, 2011, now U.S. Pat. No. 8,728,764, which is a National Stage of International Application No. PCT/GB2009/002366 filed Oct. 2, 2009, which claims the priority of U.S. Provisional Application No. 61/102,232, filed on Oct. 2, 2008. The contents of each of these applications are hereby incorporated by reference in their entireties.

FIELD OF THE INVENTION

The present invention relates to the field of molecular biology, and more specifically to methods for reducing the complexity of a nucleic acid sample.

BACKGROUND TO THE INVENTION

The draft sequence of the human genome was published in 2001 by the Human Genome Consortium (Nature Vol 409; issue 6822) and Celera Genomics (Science, Vol 291, issue 5507, 1304-1351). Capitalizing on this investment and realizing the potential of the Human Genome Project requires a better understanding of genetic variation and its effect in disease.

It has been estimated that any two copies of the human genome differ from one another by as little as 0.1% —in other words, a total of three million variants, or one variant every 1000 bases over a total of three billion that make up the human genome. Since such variation can affect disease susceptibility and responses to drugs, it is essential to identify the genetic factors which contribute to biological variation. DNA sequencing is a fundamental tool enabling the screening of genes for such genetic mutations associated with disease. High throughput and high accuracy sequencing methods are therefore required to screen the complete genome sequence of an animal in order to identify unique nucleic acid sequences, which may indicate the presence of or predisposition to various physiological or pathological conditions.

DNA sequencing of large and complex genomes is currently limited by cost. With a significant proportion of human genomic DNA comprising repetitive sequences, reducing the sequence complexity of the sample of genomic DNA reduces the amount of sequencing required. Furthermore, with prior genetic information, it is possible to correlate a phenotype, such as a predisposition to a disease, with the genetic variation of one or more regions of the genome. What is desired is the application and advantages of high throughput sequencing methods specifically to these regions of interest among many individuals. In addition, in certain circumstances, it is desirable to generate a 'genome-wide' analysis of a particular genomic feature, such as an exon, to correlate genetic diversity in the protein-coding regions across many individuals.

Consequently, there is a need for targeted sequencing of gene-rich regions that can provide an alternative approach to whole genome sequencing.

SUMMARY OF THE INVENTION

The present invention provides pools of oligonucleotide probes and related methods. The pools can comprise probes to be amplified on a solid surface and then cleaved, thereby providing arrays of paired primers.

The invention also provides methods for selecting a portion of a nucleic acid sample by hybridisation of the sample to an array and amplification to selectively enrich the sample for sequences of interest, which can then be sequenced.

The invention also provides methods for analysing nucleic acid samples on an array prepared by amplifying the pool of oligonucleotide probes.

BRIEF DESCRIPTION OF THE DRAWINGS

FIG. 4 shows an alternative use of the presynthesised oligonucleotide sequences for high throughput genotyping.

DETAILED DESCRIPTION OF THE INVENTION

Figure 1:
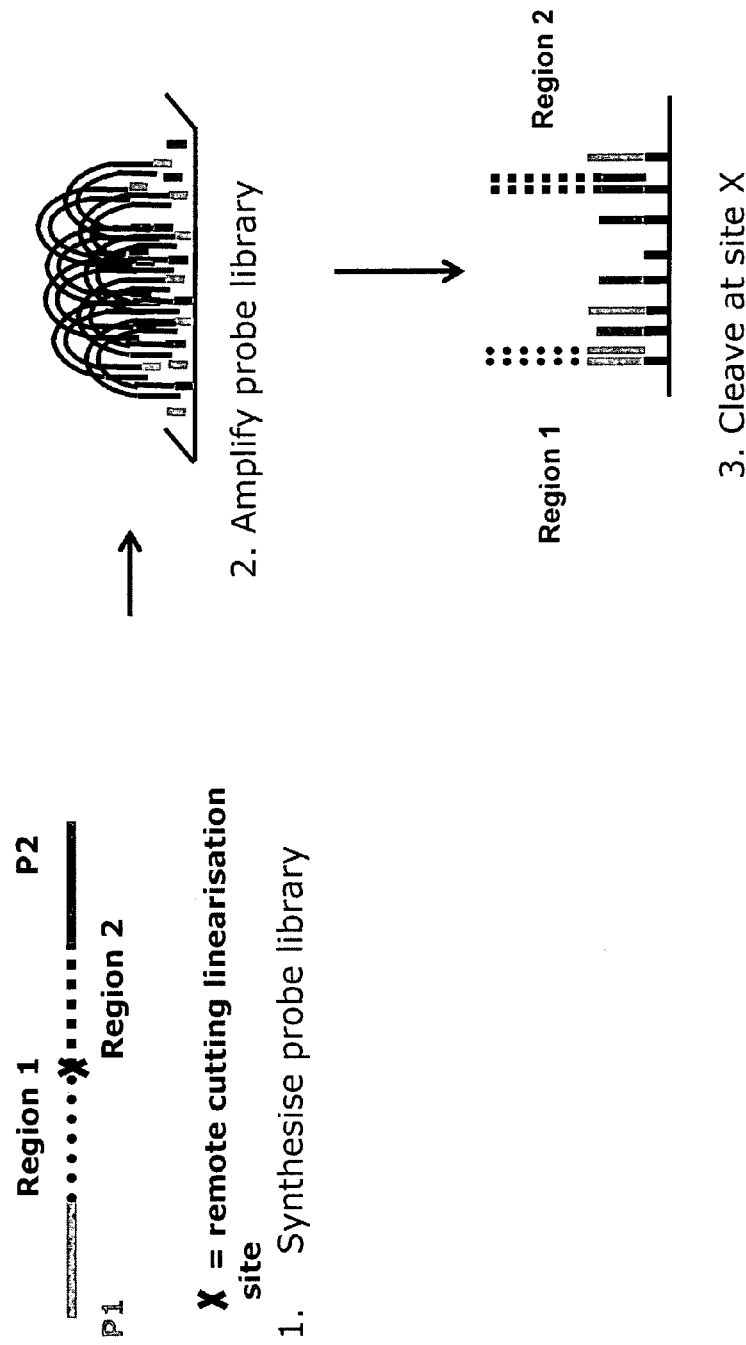
FIG. 1 shows a schematic for the preparation of an array of primer pairs by amplification and cleavage of a mixture of presynthesised oligonucleotide sequences.

A number of non-electrophoretic 'next generation' sequencing technologies rely on the massively parallel analysis of millions of short nucleic acid fragments. In some instances, the nucleic acid samples may be separated to the level of isolated single templates and then amplified prior to sequencing. The amplification may be carried out in the form of single templates attached to a population of individual beads, which can be amplified, for example, in individual bubbles of an emulsion or in discreet wells, or may be carried out on fragments immobilised to a planar surface to form an array of amplified nucleic acid clusters. Rather than amplifying the whole of a nucleic acid sample prior to sequencing, the methods of the present invention describe a two-stage amplification process that results in a preselected portion being preferentially amplified.

Probes and Probe Libraries

In one embodiment of the method of the invention, the method commences with a first amplification using a pool or library of pre-prepared probes which can be used to select for regions of interest from the nucleic acid sample.

Genomic DNA can be characterized by regions of highly repetitive sequence, and thus removal of 50% of the material in the sample, for example, may only lose 10% of the variation between two samples. In order to sample widely across the whole expressed region of the human genome, about 3% of the total bases, or 10 million bases (or base pairs, where appropriate) of sequence can be sampled, which could equate to 50,000 regions of 200 base pairs, for example. A probe library pool could therefore be designed to comprise approximately 50,000 oligonucleotide sequences, where each sequence comprises two regions, which are complementary to two pre-determined regions of the sample spaced 200 base pairs apart, for example.

The number of probe sequences may be selected based on the complexity level of the sample material and the sequence length desired to be sequenced. For example, to select out a single region of 10,000 bases may require 50 probes with a 200 base pair gap, 100 probes with a 100 base pair gap or 10 probes with a 1000 base pair gap. In order to fully resequence the whole 10,000 base region, the whole gap between the probes would need to be sequenced, so the gap can be designed to reflect the length of reads obtainable in the sequencing process used to analyse the sequence.

The term 'probe library' or 'probe sequences' refers to the nucleic acid strands used to perform any one embodiment of the invention. A probe library, or pool can comprise greater than $10^2$, $10^3$, $10^4$, $10^5$, or $10^6$ or more different probe sequences. The probe libraries or probe sequences may comprise a number of features, or sub-regions, of nucleic acid sequence used to perform certain aspects of the inventions as further described below. The probe library may be prepared by synthesising each of the probe sequences separately and pooling the individual probes. Alternatively the probe library may be prepared using a solid support such as a microarray to synthesise the probes on discreet areas of the support. The probe library may be cleaved from the array using a cleavable linkage. Synthesis of the probe library may be carried out using array synthesis methods as described in application US20090036660, the contents of which are incorporated herein by reference in their entirety. The term 'pool of oligonucleotide probes' is used interchangeably with 'probe library' to refer to a collection of probe sequences used in any particular embodiment of the invention.

The probes may be designed such that the 5' ends and the 3' ends carry a region of universal sequence. 'Universal sequence' means a region of sequence that is common to two or more nucleic acid molecules where the molecules also have regions of different sequence. A universal sequence at both ends of a collection of molecules may serve as a convenient site for the hybridisation of a primer to enable the amplification of multiple different sequences using a single primer pair complementary to the universal sequence. Thus a 'universal primer' is a priming sequence that can hybridise to a universal sequence. In addition, the universal sequences may be the same, or complementary to, a sequence immobilised to a solid support. Such universal ends allow for universal amplification of the whole probe mixture using the same set of sequences.

The probes may also contain one, two or more regions of sequence that allow for selection of the desired portion of the target sample. 'Regions of sequence that allow for selection' as used herein means an oligonucleotide sequence that is designed and fabricated in order to hybridise to a known region of a nucleic acid sample. The physical material may derive from a chemically synthesied oligonucleotide, or an amplified copy thereof, or may originate from a biological sequence, for example a PCR fragment of a region between two priming sequences, an expressed gene, an artificial chromosome such as BAC or YAC, or other similar material.

In one embodiment, the probe library pool may comprise a single region for selection. In this embodiment, the probe amplicons may be exposed to fluorescently labelled reagents, in order to work out both the sequences of the regions for selection, and the identity of one or more of the bases in the nucleic acid sample. The sequences of the region for selection can be decoded using cycles of hybridisation and removal of fluorescently labelled oligonucleotides, or may be determined using sequencing methods. The decoded array may be used in further assays, for example primer extension against a hybridised nucleic acid sample or hybridisation to a pre-labelled oligonucleotide or nucleic acid sample.

In another embodiment, first and second regions of the probe are used in the invention to hybridise to the nucleic acid sample, and may be defined as region one and region two (or the first and second known regions). Region one and region two may be originally connected together in a single probe sequence, but may be separated by the cleavage step described below. Upon cleavage, the two regions remain in the same feature on the solid support, but are not directly connected together as part of a single nucleotide strand.

The gap between the two selected regions in the sample of interest may be from a few base pairs up to 5000 base pairs or more. The gap size may be from 10 base pairs to 2000 base pairs, or 50-500 base pairs. In a particular embodiment, the gap size may be from any combination of 50, 75, 100, 125, 150, 175, 200, or 225 base pairs to 150, 200, 250, 300, 350, 400, 450 or 500 base pairs in length.

Examples of Probe Design

Probe sequences may be designed to include a single region for selection located between universal primer sequences, or the probe sequences may be designed to include two regions for selection, which may be linked in a way that is cleavable. A number of exemplary designs for the probe library are set out below, but these are not limiting and are included merely for illustrating various embodiments of the invention:

Key to Terminology:
Universal primer sequence=P1, P2
First and Second Known Regions for selection=R1, R2
Cleavage site=X
Additional bases of n+1 length/sequence=N(n)N
Design 1 (for MmeI Cleavage)

```
5'-P1 -TCCAAC-R1- X-R2 -GTTGGA-P2'-3'

3'-P1'-AGGTTG-R1'-X-R2'-CAACCT-P2 -5'
```

As discussed above, using MmeI cleavage will result in R1 and R2' being 20 bases in length.

In this design, each single-stranded probe amplicon comprises from the 5' end, a first universal sequence (P1), a first recognition sequence for a remote cutting restriction endonuclease (TCCAAC), a first region for selection (R1), a second region for selection (R2), a sequence complementary to the first recognition sequence (GTTGGA) and a second universal sequence (P2').

The first and second universal sequences may be of different length and/or sequence to each other, but common to other members of the library. They may be non-complementary to regions of the nucleic acid sample in order to prevent undesired cross-hybridisation. The universal sequences may be between 20-40 base pairs in length, and may be of sufficient length to remain hybridised during a polymerase extension reaction using a thermophilic DNA polymerase, at for example 72° C.

The self complementary copy of the sequence is defined by the Watson-Crick pairing rules, therefore for the MmeI sequence TCCAAC, the self complementary sequence would be 5'-GTTGGA, and for the EcoP15I sequence CAGCAG, the self complementary sequence would be 5'-CTGCTG.

In selected applications where the probes are cleaved using restriction enzymes, the length of region for selection one and region for selection two is defined by the choice of restriction enzyme used to cleave the probe amplicons. This may be between, for example 5-100 base pairs. The region may be between 12-25 bases. The length may be adjusted to compensate for the complexity of the nucleic sample. For example, a sequence of 12 bases may be long enough to specifically select out the desired regions from a bacterial genome of a few million bases, whereas longer regions of 25 bases may be required to specifically select for human samples.

Design 2 (for Single MboI Cleavage)

```
5'-P1 -R1-X-GATC- -R2 -P2'-3'

3'-P1'-R1'- CTAG-X-R2'-P2 -5'
```

In this example, each single stranded probe amplicon comprises from the 5' end, a first universal sequence, a first region for selection, a single recognition site for a restriction endonuclease which cuts adjacent to the 5' side of the site, a first recognition sequence for a remote cutting restriction endonuclease, a second region for selection and a second universal sequence.

There may additionally be a second restriction endonuclease site. The universal sequences are defined as for Design 1. The recognition site(s) should allow cleavage of the strand such that none of the recognition site remains on the 5' side of the site after cleavage. The cleavage may be immediately adjacent to the recognition site, or may be one or more bases away on the 5' side of the site. The use of a single site, which may be 4 or 5 bases in length, for example as shown for MboI, which requires a 4 base site GATC. Other suitable enzymes which cut on the 5' side of their recognition sites may include BssKI (CCNGG), DpnII (GATC), Hpy99I (CGACG or CGTCG), NlaIII (CATG), PspGI (CCAGG or CCTGG), Sau3AI (GATC), StyD4I (CCNGG), and Tsp45I (GTCAC or GTGAC)

Using this process, R1 and R2 can be any length, and may be of different lengths for different probe amplicons. After cleavage, the 5' ends of the strands do not carry any extra sequence to P1 and R1, or R2 and P2', wherein P1 and P2' are universal sequences and R1 and R2 are regions for selection.

Design 3 (for Double Cleavage with MboI & NlaIII)

```
5'-P1 -R1-X-GATC- -N(n)N- -CATG-X-R2 -P2'-3'

3'-P1'-R1'- CTAG-X-N(n)N-X-GTAC- -R2'-P2 -5'
```

In this design, a single-stranded probe amplicon comprises from the 5' end, a first universal sequence, a first region for selection, a first recognition site for a restriction endonuclease which cuts adjacent to the 5' side of the site, a recognition site for a restriction endonuclease which cuts adjacent to the 3' side of the site, a second region for selection and a second universal sequence. Secondly, a single stranded probe amplicon comprises from the 5' end, a first universal sequence, a first region for selection, a first recognition site for a restriction endonuclease which cuts adjacent to the 3' side of the site, a recognition site for a restriction endonuclease which cuts adjacent to the 5' side of the site, a second region for selection and a second universal sequence.

The probe amplicons may additionally comprise further bases between the two endonuclease recognition sites. The use of two different recognition sites means that all extraneous bases can be removed from a single strand. Any combination of the enzymes used in Design 2 may be applicable to a construct of this type.

Using this process, R1 and R2 can be any length, and after cleavage at sites X, the top strand does not carry any extra bases other than P1, R1, R2 and P2'. Again R1 and R2 can be different lengths for different members of the library mixture.

Immobilisation of Primers

Primers for solid-phase amplification may be immobilised by single point covalent attachment to the solid support at or near the 5' end of the primer, leaving the template-specific portion of the primer free to anneal to its cognate template and the 3' hydroxyl group free for primer extension. Any suitable covalent attachment means known in the art may be used for this purpose. The chosen attachment chemistry will depend on the nature of the solid support, and any derivatisation or functionalisation applied to it. The primer itself may include a moiety, which may be a non-nucleotide chemical modification, to facilitate attachment.

In a particular embodiment, the primer may include a sulphur-containing nucleophile, such as phosphorothioate or thiophosphate, at the 5' end. In the case of solid-supported polyacrylamide hydrogels (as described below), this nucleophile will bind to a bromoacetamide group present in the hydrogel. A more particular means of attaching primers and templates to a solid support is via 5' phosphorothioate attachment to a hydrogel comprised of polymerised acrylamide and N-(5-bromoacetamidylpentyl) acrylamide (BRAPA), as described more fully in publication WO 05/065814.

Certain embodiments of the invention may make use of solid supports comprised of an inert substrate or matrix (e.g. glass slides, polymer beads, etc) which has been "functionalised", for example by application of a layer or coating of an intermediate material comprising reactive groups which permit covalent attachment to biomolecules, such as polynucleotides. Examples of such supports include, but are not limited to, polyacrylamide hydrogels supported on an inert substrate such as glass. In such embodiments, the biomolecules (e.g. polynucleotides) may be directly covalently attached to the intermediate material (e.g. the hydrogel), but the intermediate material may itself be non-covalently attached to the substrate or matrix (e.g. the glass substrate). The term "covalent attachment to a solid support" is to be interpreted accordingly as encompassing this type of arrangement.

Examples of solid phases, or surfaces, may be a planar array made from, for example, glass, silica or plastic microscope slides or similar materials, beads or an array of beads on a surface. The surface may additionally comprise one, two or more immobilised primers.

Clustered arrays can be prepared using either a process of thermocycling, as described in publication WO 98/44151, or a process whereby the temperature is maintained as a constant, and the cycles of extension and denaturing are performed using changes of reagents. Such isothermal amplification methods are described in publication WO 02/46456 and U.S. Publication 2008/0009420 (Isothermal methods for creating clonal single molecule arrays), which are incorporated herein by reference in their entirety.

Amplification of Probe Libraries

For some embodiments of the invention, the method requires that the pool of oligonucleotides are amplified, for example on a solid support.

In one embodiment, the individual oligonucleotide members of the probe library can be spatially separated from one another prior to amplification, thus the amplification results in multiple copies of each individual oligonucleotide that are separated from the copies deriving from a different oligonucleotide. Such clonal amplification results in a collection of probe amplicons where at least a proportion of the members of the collection of probe amplicons contain multiple copies of a single sequence. As used herein, the term 'probe amplicon' refers to an oligonucleotide that has been amplified or copied from an oligonucleotide probe or portion thereof. The individual isolated nature of each amplification thus gives a method of performing 'multiplex amplification' of different oligonucleotides as templates for probes.

If the probe library is amplified on a planar surface, then an array of nucleic acid clusters can be produced. The amplification of the probe libraries can thus be used to produce an array of first clusters on a solid support.

However, the term clusters should not be taken as limiting to only a planar surface; a nucleic acid template amplified on a bead or microsphere is also considered as a cluster for the purposes of the invention. The amplification process gives rise to a high density of features wherein each feature comprises multiple copies of a double-stranded sequence, or to a large number of beads carrying multiple copies of a single sequence.

Specific details useful in the invention are further described in detail below. U.S. Pat. No. 7,115,400 or U.S. Publication 2005/0100900 both describe methods of forming polynucleotide arrays based on 'solid-phase' nucleic acid amplification, which is a bridging amplification reaction wherein the amplification products are immobilised on a solid support in order to form arrays comprised of nucleic acid clusters or 'colonies'. Each cluster or colony on such an array is formed from a plurality of identical immobilised polynucleotide strands and a plurality of identical immobilised complementary polynucleotide strands. The arrays so-formed are generally referred to herein as 'clustered arrays' and their general features will be further understood by reference to patent documents WO 98/44151, WO 00/18957, U.S. Pat. No. 7,115,400 or U.S. Publication 2005/0100900, each of which are incorporated herein in their entirety by reference. One aspect of the invention as described herein relates to amplifying a probe library in the form of a pool of synthetic oligonucleotides. The synthetic oligonucleotides comprise regions of universal sequence at each end, and one or more regions of target for selection of a target sequence.

Cleavage of Probes

As discussed above, the two or more regions in a probe can be connected in a way that allows separation of the two regions for selection after a first amplification reaction. 'Connected in a way that allows separation' as used herein means that the probes are capable of being selectively cleaved at a defined location. The cleavage may be sequence-specific or may be independent of sequence in order to make use of multiple regions of different sequence that allow for selection of multiple regions from the sample.

Accordingly, after an amplification reaction, the nucleic acids may be present in the form of duplexes where the 5' ends of both strands are attached to the surface. The probe amplicons may then be treated to one or more cleavage reagents, under suitable cleavage conditions in order to selectively cleave the probe amplicons and separate the two regions for selection.

To allow multiplexing of different sequences, the cleavage into two fragments may be carried out in a way that is independent of the sequence of the cleavage site. The cleavage of the single strand into two primers can be carried out by, for example, the use of a restriction endonuclease that cuts remotely from its recognition site. The recognition sequence for the restriction endonuclease is defined by the choice of enzyme, which is defined by the desired length of the region used for selection. The recognition sequence may be 4-8 bases in length. The first sequence may be, for example CAGCAG in order to use EcoP15I, or TCCAAC in order to use MmeI. The recognition sequences for other restriction endonucleases are known in the art. Thus, a method described herein can include a step of cleaving a nucleic acid with a type IIs, type III, or other restriction endonuclease that cuts remotely from its recognition site.

A large number of such type IIs or type III enzymes are known. The restriction enzyme may be selected to have as great a reach into the fragment as possible. Enzymes such as, for example MmeI, which cuts 18/20 base pairs remotely from its 6 base pair recognition site, would generate immobilised region one and region two primers of about 20 base pairs each. The length of the primer can be extended by the use of enzymes which cut further away from their binding site, such as for example EcoP15I, which would give region one and region two primers of 25 base pairs. Further examples of restriction enzymes which cut remotely to their binding site include AcuI, AlwI, BbvI, BccI, BceAI, BciVI, BfuAI, BmrI, BpmI, BpuEI, BseRI, BsgI, BsmFI, BspMI, BtgZI, EciI, FokI, HgaI, HphI, HpyAV, MboII, MlyI, MnlI, NmeAIII, PleI and SfaNI.

Alternatively or additionally the strand cleavage can be carried out by the use of endonucleases that cleave a nucleic acid either internally or adjacent to their particular recognition sequences. Such endonucleases, when used to treat the probe amplicons, can remove their recognition sequences from the probe amplicons. For example, a restriction endonuclease that cuts on the 5' side of both strands will leave no trace of its recognition site on the 5' immobilised strands. The probe strands may carry a single site for cleavage, or two or more sites. The method of the invention may therefore include a step of cleaving the probe amplicon at a single site or at two or more sites. The two or more sites may have the same or different recognition sequence. The probe amplicons may comprise additional nucleotides between the region one and region two sequences, as long as these bases detach themselves from the immobilised sequences.

Primer Pairs

Although the three designs shown above are not meant to be limiting, they illustrate how, after amplification of a pool of oligonucleotide probes on a surface, cleavage of the amplified probes can generate into pairs of two 'primers', as shown in FIG. 1.

An array prepared in this manner provides pairs of primers specific to each assay that are co-located in the same vicinity. Thus a first cluster comprises primer pairs A and B, a second cluster primer pairs C and D, etc. If primers A, B, C and D were simply mixed and spread on a surface, then the primer pairs A and B would not necessarily be co-located in the same confined area: the whole surface would be a homogeneous mixture of all four sequences. The use of the in-situ amplification and cleavage method to co-locate primer pairs is a significant improvement over previous methods of spotting a large number of pairs of primers from solution, not least because the ratio of primers in each location will essentially be 1:1. In contrast to spotting methods, there is no need to measure the ratio of the two primers in each of the solutions spotted onto the surface, as the two primers derive from a single species that is cleaved into two fragments. The array of clusters of paired primers thus produced is one feature of the invention.

In summary, the present invention provides a method for selecting a portion of a nucleic acid sample by
  a) providing a probe library comprising a pool of oligonucleotides of different sequences, wherein each member of the probe library comprises a universal sequence at the 3' end that is common to the probes in the library, a first known region capable of hybridising to a preselected region of the nucleic acid sample of interest, a second known region capable of hybridising to a second pre-selected region of the nucleic acid sample in the vicinity of the first known sequence, a universal sequence at the 5' end that is common to the probes in the library, and a site for selectively cleaving the oligonucleotide strand between the first and second known regions;

b) separating the individual molecules of the probe library and amplifying the separated individual molecules in parallel to form a collection of probe amplicons where each member of the collection contains multiple copies of a single sequence;

c) cleaving the probe amplicons to disconnect the first and second known regions; and thereby providing an array of primer pairs on a solid support.

Use in Subsequent Assays

The array of primer pairs may then be used in a number of subsequent assays on a nucleic acid sample. 'Subsequent assays' as used herein means any assay that may be performed on the selected nucleic acid sample. Examples include sequencing of the selected fragments, or analysis by ligation or by hybridisation. Where the method involves hybridising a nucleic acid sample to probes immobilised on a surface, as discussed in greater detail below, any assay capable of being performed on an immobilised nucleic acid is within the scope of the invention.

Figure 2:
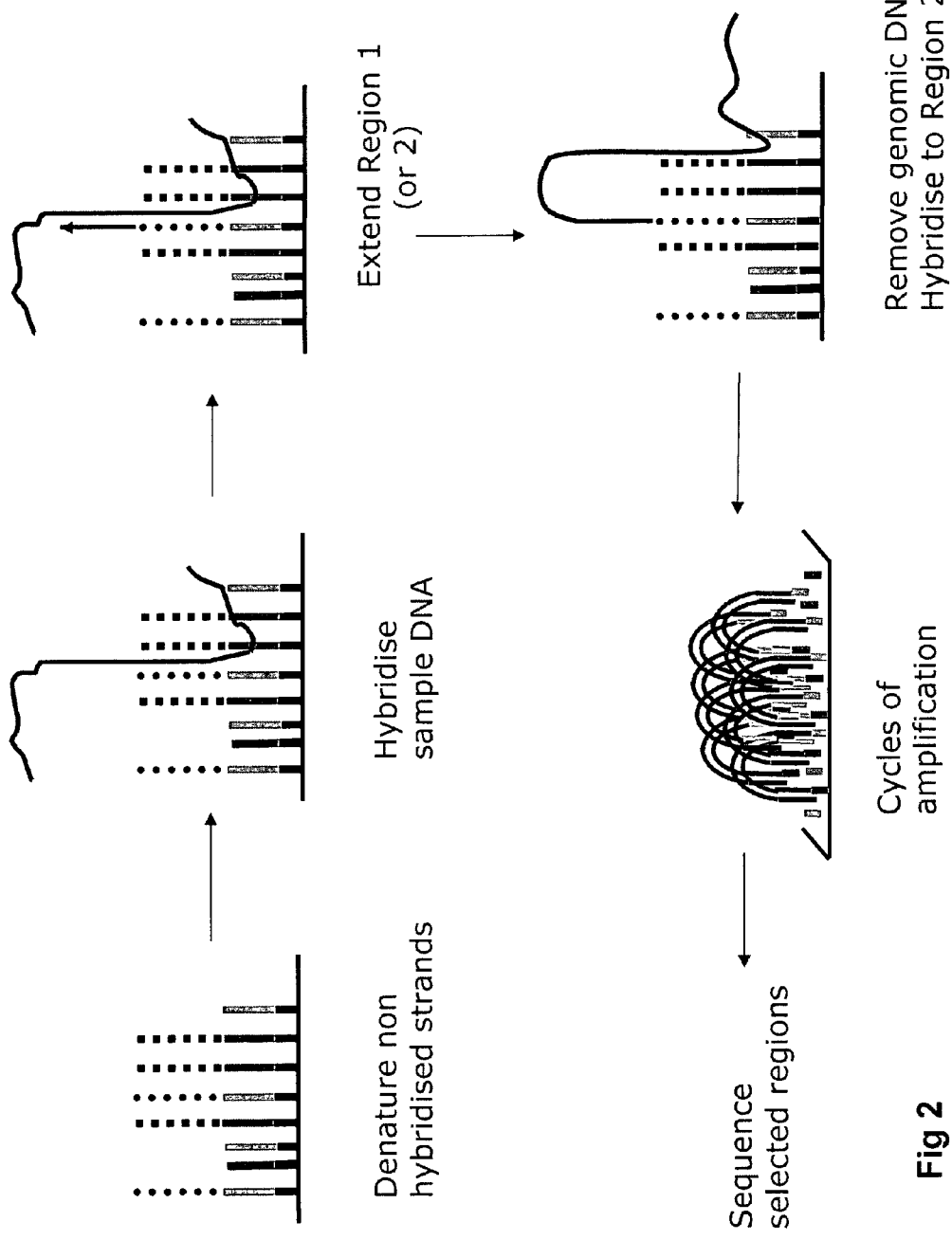
FIG. 2 Shows the use of the array of primer pairs for region-specific amplification of pre-selected regions of interest in a nucleic acid sample for sequencing.
Figure 3:
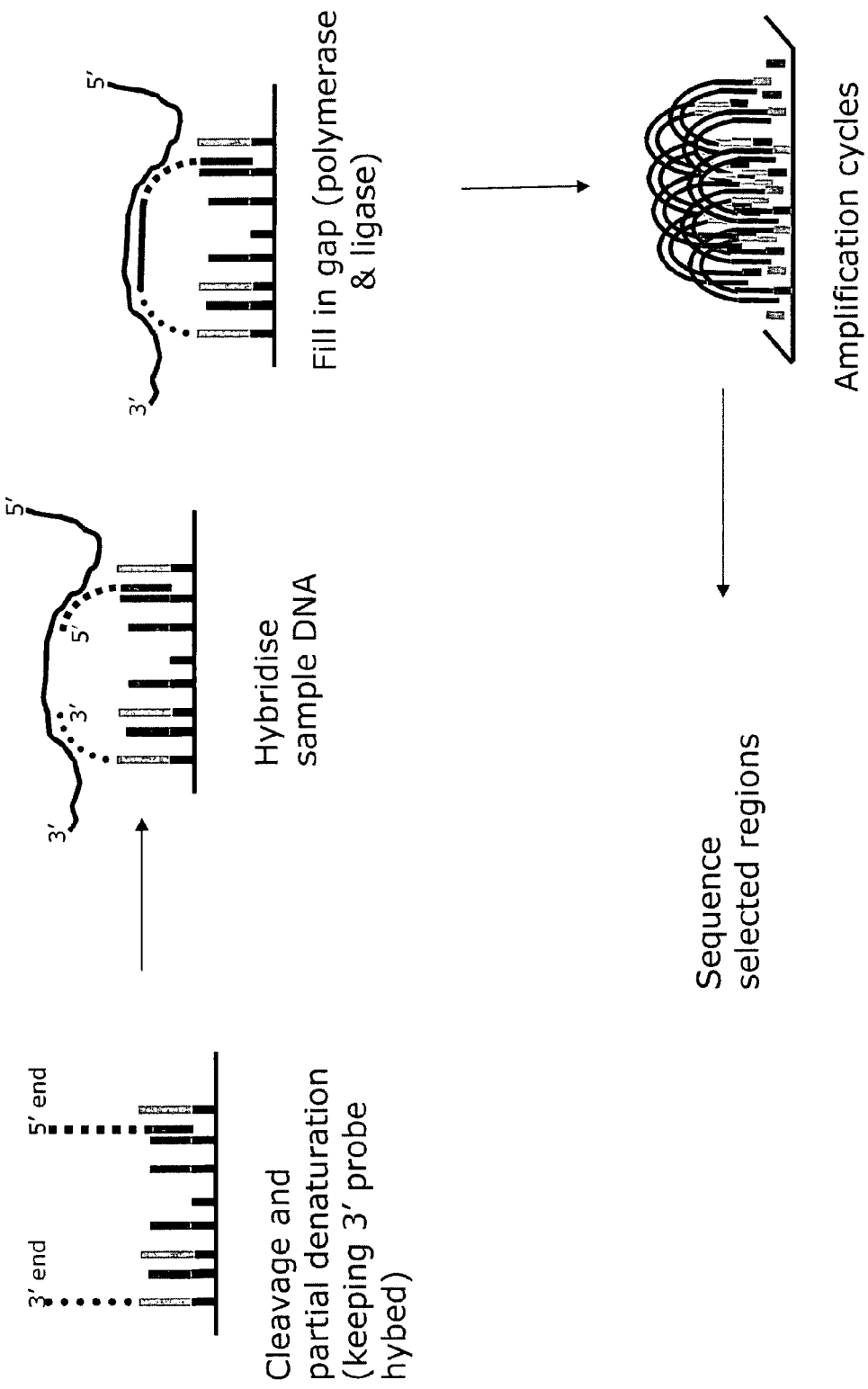
FIG. 3 Shows the use of the array of primer pairs for a high-throughput ligation and sequencing assay to select for regions of interest in a nucleic acid sample for sequencing.

In one aspect of the invention the primer pairs may be utilised for the multiplex amplification of selected regions of the nucleic acid sample, as shown in FIG. 2. In another aspect the primer pairs may be utilised in a high throughput ligation based assay as shown in FIG. 3.

In another embodiment, the nucleic acid sample may undergo a multiplexed reaction in solution, for example a polymerase extension or ligation reaction, which generates fluorescently labelled material and can be hybridised to the probe amplicons on the array. 'Multiplex amplification' as used herein means the ability to amplify molecules with different nucleic acid sequences simultaneously in the same reaction. The amplification may be performed using a single pair of primers complementary to a universal sequence, or may be multiple primer pairs complementary to different sequences. Amplification of different sequences in different bubbles of a single emulsion reaction is within the scope of the invention.

Nucleic Acid Samples

The terms 'target nucleic acid sequence', 'target nucleic acid molecule', 'target nucleic acid' and 'target nucleic acid fragment' may be used interchangeably to refer to nucleic acid molecules or sequences that it is desired to sequence on an array according to the invention. The target nucleic acid sequence may be originate from a nucleic acid sample of interest. The nucleic acid sample of interest comprises the primary polynucleotide molecules, which may further comprise one or more specific regions of interest, or target nucleic acid sequences, which may comprise sequences complementary to one or more of the known regions in the pool of probes. The target nucleic acid may be essentially any nucleic acid which comprises at least one region of known sequence. It may be, for example, a fragment of genomic DNA or cDNA. Sequencing may result in determination of the sequence of the whole, or a part of the target molecule. The targets can be derived from a primary nucleic acid sample. The target nucleic acid sequences may comprise the first and second pre-selected regions of interest from the primary polynucleotide sequences, plus a sequence between the two regions. The number of target regions may correlate with the number of probe sequences in the library, such that each different probe sequence selects a different target sequence. The primary nucleic acid from which targets are derived can first be randomly fragmented. The targets can also be obtained from a primary RNA sample by reverse transcription into cDNA.

As used herein, the term 'polynucleotide' refers to deoxyribonucleic acid (DNA), and ribonucleic acid (RNA).

The terms should be understood to include, as equivalents, analogs of either DNA or RNA made from nucleotide analogs and to be applicable to single stranded (such as sense or antisense) and double stranded polynucleotides. The term as used herein also encompasses cDNA, that is complementary or copy DNA produced from an RNA template, for example by the action of reverse transcriptase.

The primary polynucleotide molecules may originate in double-stranded DNA (dsDNA) form (e.g. genomic DNA fragments, PCR and amplification products and the like) or may have originated in single-stranded form, as DNA or RNA, and been converted to dsDNA form. By way of example, mRNA molecules may be copied into double-stranded cDNAs suitable for use in the method of the invention using standard techniques well known in the art. The precise sequence of the primary polynucleotide molecules may be known or unknown.

The nucleic acid sample can be an initial sample of unenriched genomic DNA. As an example of genomic DNA useful as a nucleic acid sample, a human genome consists of approximately 3.1 billion bases of sequence. Exemplary size estimates for other genomes that can be used in the invention are about 2.7 Gbp (mouse), 2.8 Gbp (rat), 1.7 Gbp (zebrafish), 165 Mbp (fruitfly), 13.5 Mbp (*S. cerevisiae*), 390 Mbp (fugu), 278 Mbp (mosquito) or 103 Mbp (*C. elegans*). Those skilled in the art will recognize that genomes having sizes other than those exemplified above including, for example, smaller or larger genomes, can be used in a method of the invention.

In a particular embodiment, the primary polynucleotide molecules are DNA molecules. More particularly, the primary polynucleotide molecules represent the entire genetic complement of an organism, and are genomic DNA molecules which include both intron and exon sequences (coding sequence), as well as non-coding regulatory sequences such as promoter and enhancer sequences. Particular subsets of polynucleotide sequences or genomic DNA can also be used, such as particular chromosomes. Yet more particularly, the sequence of the primary polynucleotide molecules or a portion thereof can be a target sequence. Still yet more particularly, the primary polynucleotide molecules are genomic DNA molecules, from example human, mammalian, bacterial, fungal or plant genomic DNA.

The primary polynucleotide molecules may be treated chemically or enzymatically either prior or subsequent to any random fragmentation processes, and prior to or subsequent to the step of enrichment using the probe libraries or probe amplicons. In the methods described herein, the nucleic acid samples may be fragmented prior to hybridisation on the array, or may be used without fragmentation. The samples may be subjected to anamplification prior to use, for example a whole sample amplification technique such as random primer extension.

"Random fragmentation" refers to reducing the length of a polynucleotide molecule in a non-ordered fashion, for example, by enzymatic, chemical or mechanical means. Such fragmentation methods are known in the art and can utilise standard methods (Sambrook and Russell, Molecular Cloning, A Laboratory Manual, third edition). Moreover, random fragmentation is designed to produce fragments irrespective of the sequence identity or position of nucleotides comprising and/or surrounding the break. More particularly, the random fragmentation can be by mechanical means such as nebulisation or sonication. The fragments can be about 50 base pairs in length to about 1500 base pairs in length, still more particularly 50-700 base pairs in length, yet more particularly 50-400 base pairs in length. Most particularly, the method is used to generate smaller fragments of from 100-300 base pairs in length.

The methods as described herein may be used to remove nucleic acid strands that it is not desired to sequence, rather than to specifically amplify only the sequences of interest. At the level of the whole genome, reduction of 50% of the DNA sample complexity can result in a two-fold reduction in the cost and time of sequencing the remaining regions of biological interest. The methods as described herein can also be used to select large regions of a genome (eg megabases) for resequencing of multiple individuals, or can select out all the exons from a genomic sample. As a further advantage, a single pool of oligonucleotides can be used to process multiple samples of interest, and thus the costs of the oligonucleotide synthesis can be amortised over many individual samples.

The term 'enrichment' refers to the process of increasing the relative abundance of particular nucleic acid sequences in a sample relative to the level of nucleic acid sequences as a whole initially present in said sample before treatment. Thus the enrichment step provides a relative percentage or fractional increase, rather than directly increasing, for example, the absolute copy number of the nucleic acid sequences of interest as other amplification methods, such as PCR, would. After the step of enrichment, the sample to be analysed may be referred to as an enriched, or selected nucleic acid sample.

The level of complexity reduction obtainable by enriching a genomic sample may enable reduction of 10%, 20%, 30%, 40%, 50%, 60%, 70%, 80%, 90%, 95%, or 99% of the sequence of the genome sample, or may involve selection of only a few percent of the genome, or even a few thousand base pairs. The sample may be reduced from 3 billion base pairs to 10 million base pairs or less, depending on the size of the initial genome and the level of reduction required. Thus, highly repetitive DNA sequences which comprise, for example 40% of human genomic DNA, can be removed quickly and efficiently from a complex population.

Region-Specific PCR

FIG. 2 Shows the use of the array of primer pairs for region-specific amplification of pre-selected parts of a nucleic acids sample. One method of the invention as shown in FIG. 2 therefore comprises a method for selecting and analysing specific regions of a nucleic acid sample, the method comprising:
 a) hybridising the nucleic acid sample to the first known sequences of the array of primer pairs;
 b) extending the first known sequences using the immobilised nucleic acid sample as a template to produce extended immobilised nucleic acid strands wherein each extended strand comprises a region complementary to the second known sequence;
 c) removing the nucleic acid sample from the surface by denaturing the extended duplexes;
 d) hybridising the extended duplexes to the oligonucleotides comprising the second known region;
 e) extending the second known region to form a duplex immobilised at both ends comprising both the first and second known regions;
 f) amplifying the immobilised duplexes; and
 g) obtaining sequence information on a region between the first and second known sequences, thereby selecting and analysing specific regions of the nucleic acid sample.

In particular embodiments, the oligonucleotide probes used in the first amplification are designed to carry two sequences that are known to be in close proximity in the target sample. For example, when performing PCR amplification using a pair of primers, the primers usually hybridise to two regions of a nucleic acid sample that are less than 10,000 bases apart. For the current application, the two sequences may be less than 5000 bases apart, or less than 1000 bases apart. The sequences may be 50-500 bases apart. Thus upon extension of the primer hybridised to the nucleic acid target sequences (as with PCR), a sequence that hybridises to the second primer is produced. The phrase 'in close proximity' therefore refers to two sequences that are capable of amplification using a pair of synthetic primers which hybridise to those sequences.

A nucleic acid sample of interest may hybridise to both the first and second known regions on the array. Upon extension opposite the template sequence, sequences complementary to the second and first primers respectively are synthesised. The hybridised templates may be removed to leave extended immobilised sequences which contain both the first and second known regions. The extended strands may be amplified in a second amplification reaction to synthesise a second pool of nucleic acid clusters in the same locations as the first clusters on the surface. The second pool of clusters have sequences deriving from the first and second known regions from the first pool of clusters plus the additional sequences that come from the regions between the two selected target sequences. These clusters can be amplified from one or more target molecules, as the hybridisation step should select out only the correct sequences, and therefore the amplification uses multiple different priming sequences rather than universal priming sequences. Each region for selection in the probe amplicons can be used to hybridise to multiple copies of its complementary target sequence. As each feature in the array of primer pairs comprises a region for selection of a different target region from a nucleic acid sample, then the selected regions between the primer pairs are also different for different features on the array.

The arrays are particularly useful for high-throughput or multiplex embodiments. In one embodiment of the invention, shown in FIG. 3, the cleaved known regions created by cleaving the probe amplicons in the first clusters are treated differently to the multiplex amplification procedure shown in FIG. 2. In order to amplify material, the 5' end of each strand of the double stranded probe amplicon is needed, and hence, as shown in FIG. 2, the non-hybridised material is simply removed from the surface after cleavage of the probe amplicon. However, in order to carry out an assay based on extension and ligation, for example as shown in FIG. 3, both regions for selection need to hybridise to the same template strand. Therefore, rather than removing the non-hybridised material so that the 5' ends of both strands are retained, the cleaved probe amplicons are treated such that the 5' end of one strand is retained, along with the 3' end of the same strand. This may be carried out in a number of ways, for example by modifying one of the immobilised primers to allow a second cleavage of the strand. Such a modification may be a nucleoside base analogue that allows subsequent selective removal and strand cleavage, for example deoxyuridine or 8-oxoguanine. If the primers attached to the surface carry such a modification, then treatment with uracil glycosylase/endonuclease or FPG respectively can be used to cleave the strands at the modified positions. If the length of the universal primers is much longer than the sequence of the known probe portion (for example 40 and 18 bases, respectively), then the shorter region may be selectively de-annealed whilst the 3' end of the selected target remains hybridised to the surface.

The array of 5' and 3' sequences may be exposed to a nucleic acid sample under hybridisation conditions such that both known regions hybridise to the same strand. The immobilised first region primers can be extended using the nucleic acid sample as a template, and once the extended primer meets the 5' end of the second primer, the ends can be joined. Such ligation assays are well known in the art, for example as 'Padlock probes' or in Illumina's GoldenGate assay (see, e.g., US 2003/0108900, the contents of which are incorporated herein by reference). The assays are usually performed using a non strand displacing polymerase such as Taq polymerase, and a thermostable ligase such as Taq ligase. Each cluster of probe amplicons may hybridise to one or more target molecules of the same sequence. The specific nature of the hybridisation selects for multiple copies of a single target region in each cluster. The selected multiple copies can then be further amplified, if desired.

The extended strands produced using the method shown in FIG. 3 thus contain a first and second known region from the original probe plus extra bases derived from the target samples. These extended strands can be made single-stranded and further amplified by cycles of amplification to make a second pool of clusters in the same locations as the first clusters on the surface. The second pool of clusters has sequences deriving from the known regions from the first pool of clusters plus the additional sequences that come from the selected target fragments. As each first cluster comprises a region for selection of a different target region from a nucleic acid sample, then the selected regions between the known regions are also different.

To enable the amplification reaction shown in FIG. 2 to proceed, the separated first and second known regions generated by the cleavage of the probe amplicons are typically denatured to remove the hybridised material. This may be carried out using heat treatment, or using a chemical or enzymatic denaturant, for example hydroxide, formamide or an exonuclease. The denaturation may however be carried out during the amplification reaction, for example using a helicase and a polymerase mixture.

A method of the invention can also include a step of using the separated first and second known regions to capture a region of a nucleic acid sample by hybridisation. As each cleaved probe amplicon is a different set of two primers, different cleaved amplicons will be able to hybridise to different sequences in the target sample of interest. An array of single stranded separated first and second known regions may be exposed under hybridising conditions to a target nucleic acid sample, for example a library of genomic fragments or a library of cDNA fragments. The primers on the surface can be extended using the hybridised sequences as templates.

The bases added between the two probe sequences can be determined using cycles of sequencing. Sequencing of the selected regions allows the direct sequencing of a multiplex pool of amplified products, analogous to having thousands or millions of individual PCR reactions in parallel and sequencing each PCR product in isolation.

Ligation Assay

An alternative use for the primer array is in a ligation assay, for example as shown in FIG. 3. FIG. 3 shows the use of the array of primer pairs for a high throughput ligation and sequencing assay to select regions of a nucleic acid sample for sequencing. One method of the invention as shown in FIG. 3 therefore comprises a method for selecting and analysing specific regions of a nucleic acid sample, the method comprising:

a) providing an array of primer pairs;
e) hybridising the nucleic acid sample to the first and second known sequences of the primer pairs;
f) extending the first known regions using the nucleic acid samples as templates;
g) joining the 3' ends of the extended strands to the 5' ends of the second known region to generate immobilised extended strands comprising the first and second regions;
h) amplifying the immobilised extended strands; and
i) obtaining sequence information on a region between the first and second known sequences, thereby selecting and analysing specific regions of the nucleic acid sample.

In a further alternative embodiment, the sequences of one or more of the regions for selection can be decoded, for example by hybridisation using labelled oligonucleotides, and then used to hybridise to a labelled oligonucleotide prepared in solution. In such assays the probes may be prepared having only a single region of selection between two universal sequences. The array prepared by amplifying the probes on a surface again comprises multiple copies derived from a single molecule. Thus a single probe library can be used to prepare thousands of arrays, as the library is amplified in-situ.

The array can be hybridised against a fluorescently labelled sample, or the probe amplicons can be cleaved to release known regions with a 3' hydroxyl, and that 3' hydroxyl extended with a nucleotide or oligonucleotide that is complementary to the adjacent bases in the hybridised nucleic acid target. The identity of the known regions may be deconvolved by sufficient cycles of sequencing to call the specific identity of each probe. For example if 1,000,000 probes are used, the identity of the probes may be deconvolved using 10-12 cycles of sequencing to determine the base of variation in the target, plus sufficient bases to call the location in the target sample. The methods described herein may thus be used for genotyping a nucleic acid sample. An array of probe amplicons may be prepared and hybridised with the nucleic acid sample. The hybridised nucleic acid sample may be fluorescently labelled, or the array may be labelled in order to detect the presence or identity of the sample.

Amplification and Enrichment of Nucleic Acid Sample

In common with all amplification techniques, solid-phase bridging amplification uses forward and reverse amplification primers which include 'template-specific' nucleotide sequences which are capable of annealing to sequences in the template to be amplified, or the complement thereof, under the conditions of the annealing steps of the amplification reaction. The sequences in the template to which the primers anneal under conditions of the amplification reaction may be referred to herein as 'primer-binding' sequences.

Certain embodiments of the methods described in WO 98/44151 and WO 00/18957 make use of 'universal' primers to amplify templates comprising a variable template portion that it is desired to amplify flanked 5' and 3' by common or 'universal' primer binding sequences. The 'universal' forward and reverse primers include sequences capable of annealing to the universal sequences in the template construct. The variable template portion, or 'target' may itself be of known, unknown or partially known sequence. This approach has the advantage that it is not necessary to design a specific pair of primers for each target sequence to be amplified; the same primers can be used for amplification of different templates provided that each template is modified by addition of the same universal primer-binding sequences to its 5' and 3' ends. The variable target sequence can therefore be any DNA fragment of interest. An analogous approach can be used to amplify a mixture of templates (targets with known ends), such as a plurality or library of target nucleic acid molecules (e.g. genomic DNA fragments), using a single pair of universal forward and reverse primers, provided that each template molecule in the mixture is modified by the addition of the same universal primer-binding sequences.

References herein to a particular nucleic acid sequence may, depending on the context, also refer to nucleic acid molecules which comprise the nucleic acid sequence. 'Sequencing of a target fragment' means simply that a read of the order of bases is established. The bases do not need to be contiguous, although this may be preferred, nor does every base on the entire fragment have to be sequenced. Sequencing using cycles of ligation where more than a single base varies between the ligation cassettes is within the scope of the invention, and hence every cycle of sequencing does not have to result in determination of a base for that cycle.

Sequencing of Nucleic Acid Sample

The invention also encompasses methods of sequencing the amplified nucleic acids generated by solid-phase amplification. Thus, the invention provides a method of nucleic acid sequencing comprising amplifying a selected pool of nucleic acid templates using solid-phase amplification as described above and carrying out a nucleic acid sequencing reaction to determine the sequence of the whole or a part of at least one amplified nucleic acid strand produced in the solid-phase amplification reaction.

Sequencing can be carried out using any suitable sequencing technique, such as wherein nucleotides are added successively to a free 3' hydroxyl group, resulting in synthesis of a polynucleotide chain in the 5' to 3' direction. The nature of the nucleotide added is preferably determined after each nucleotide addition. Sequencing techniques using sequencing by ligation, wherein not every contiguous base is sequenced, and techniques such as massively parallel signature sequencing (MPSS) where bases are removed from, rather than added to the strands on the surface are also within the scope of the invention, as are techniques using detection of pyrophosphate release (pyrosequencing). Such pyrosequencing based techniques can be particularly applicable to sequencing arrays of beads where the beads have been amplified in an emulsion such that a single template from the library molecule is amplified on each bead.

The initiation point for the sequencing reaction may be provided by annealing of a sequencing primer to a product of the solid-phase amplification reaction. In this connection, one or both of the known probe regions gives a known sequence which permits annealing of a sequencing primer to amplified products derived by solid-phase amplification of the regions selected from the sample.

The products of solid-phase amplification reactions wherein both forward and reverse amplification primers are covalently immobilised on the solid surface are so-called 'bridged' structures formed by annealing of pairs of immobilised polynucleotide strands and immobilised complementary strands, both strands being attached to the solid support at the 5' end. Arrays comprised of such bridged structures can provide inefficient templates for nucleic acid sequencing under typical conditions, since hybridisation of a conventional sequencing primer to one of the immobilised strands is not favoured compared to annealing of this strand to its immobilised complementary strand under standard conditions for hybridisation.

In order to provide more suitable templates for nucleic acid sequencing, it is preferred to remove substantially all or remove or displace at least a portion of one of the immobilised strands in the 'bridged' structure in order to generate a template which is at least partially single-stranded. The portion of the template which is single-stranded will thus be available for hybridisation to a sequencing primer. The process of removing all or a portion of one immobilised strand in a 'bridged' double-stranded nucleic acid structure may be referred to herein as 'linearisation', and is described in further detail in publication WO 07/010251, the contents of which are incorporated herein by reference in their entirety.

Bridged template structures may be linearised by cleavage of one or both strands with a restriction endonuclease or by cleavage of one strand with a nicking endonuclease. Other methods of cleavage can be used as an alternative to restriction enzymes or nicking enzymes, including inter alia chemical cleavage (e.g. cleavage of a diol linkage with periodate), cleavage of abasic sites by cleavage with endonuclease, or by exposure to heat or alkali, cleavage of ribonucleotides incorporated into amplification products otherwise comprised of deoxyribonucleotides, photochemical cleavage or cleavage of a peptide linker.

Following the cleavage step, regardless of the method used for cleavage, the product of the cleavage reaction may be subjected to denaturing conditions in order to remove the portion(s) of the cleaved strand(s) that are not attached to the solid support. Suitable denaturing conditions, for example sodium hydroxide solution, formamide solution or heat, will be apparent to the skilled reader with reference to standard molecular biology protocols (e.g. Sambrook et al., 2001, Molecular Cloning, A Laboratory Manual, 3rd Ed, Cold Spring Harbor Laboratory Press, Cold Spring Harbor Laboratory Press, NY; Current Protocols, eds Ausubel et al.). Denaturation results in the production of a sequencing template which is partially or substantially single-stranded. A sequencing reaction may then be initiated by hybridisation of a sequencing primer to the single-stranded portion of the template.

Thus, the invention encompasses methods wherein the nucleic acid sequencing reaction comprises hybridising a sequencing primer to a single-stranded region of a linearised amplification product, sequentially incorporating one or more nucleotides into a polynucleotide strand complementary to the region of amplified template strand to be sequenced, identifying the base present in one or more of the incorporated nucleotide(s) and thereby determining the sequence of a region of the template strand.

One preferred sequencing method which can be used in accordance with the invention uses modified nucleotides having removable 3' blocks, for example as described in WO 04/018497 and U.S. Pat. No. 7,057,026, the contents of which are incorporated herein by reference in their entirety. Once the modified nucleotide has been incorporated into the growing polynucleotide chain complementary to the region of the template being sequenced, there is no free 3'-OH group available to direct further sequence extension and therefore the polymerase can not add further nucleotides. Once the nature of the base incorporated into the growing chain has been determined, the 3' block may be removed to allow addition of the next nucleotide. By ordering the products derived using these modified nucleotides, it is possible to deduce the sequence of the DNA template. Such reactions can be done in a single experiment if each of the modified nucleotides has a different label attached thereto, known to correspond to the particular base, to facilitate discrimination between the bases added during each incorporation step. Alternatively, a separate reaction may be carried out containing each of the modified nucleotides separately.

The modified nucleotides may carry a label to facilitate their detection. A fluorescent label, for example, may be used for detection of modified nucleotides. Each nucleotide type may thus carry a different fluorescent label, for example, as described in WO 07/135368, the contents of which are incorporated herein by reference in their entirety. The detectable label need not, however, be a fluorescent label. Any label can be used which allows the detection of an incorporated nucleotide.

One method for detecting fluorescently labelled nucleotides comprises using laser light of a wavelength specific for the labelled nucleotides, or the use of other suitable sources of illumination. The fluorescence from the label on the nucleotide may be detected by a CCD camera or other suitable detection means. Suitable instrumentation for recording images of clustered arrays is described in WO 07/123744, the contents of which are incorporated herein by reference in their entirety.

The invention is not intended to be limited to use of the sequencing method outlined above, as essentially any sequencing methodology which relies on successive incorporation of nucleotides into a polynucleotide chain can be used. Suitable alternative techniques include, for example, Pyrosequencing, FISSEQ (fluorescent in situ sequencing), MPSS and sequencing by ligation-based methods, for example as described is U.S. Pat. No. 6,306,597.

The nucleic acid sample may be further analysed to obtain a second read from the opposite end of the fragment. Methodology for sequencing both ends of a cluster are described in publication WO 07/010252 and WO 08/041002, the contents of which are incorporated by reference herein in their entirety. In one example, the series of steps may be performed as follows: generate clusters, linearise, hybridise first sequencing primer and obtain first sequencing read. The first sequencing primer can be removed, a second primer hybridised and the tag sequenced. The nucleic acid strand may then be 'inverted' on the surface by synthesising a complementary copy from the remaining immobilised primers used in cluster amplification. This process of strand resynthesis regenerates the double stranded cluster. The original template strand can be removed to linearise the resynthesised strand, which can then be annealed to a sequencing primer and sequenced in a second sequencing run. Such a second read can be particularly useful in the method of the invention because sequence information is generated from both ends of the nucleic acid strand, thereby providing independent verification of the presence of pre-selected known regions of the sequence of interest, which were enriched in prior steps of the method.

In the cases where strand resynthesis is employed, both strands are typically immobilised to the surface in a way that allows subsequent release of a portion of the immobilised strand. This can be achieved through a number of mechanisms as described in WO 07/010251, the contents of which are incorporated herein by reference in their entirety. This design of primers allows control of which primer is cleaved at which point in the process, and also where in the cluster the cleavage occurs. The primers may also be chemically modified, for example with a disulfide or diol modification that allows chemical cleavage at specific locations.

Throughout this application various publications, patents patent applications, and patent publications have been referenced. The disclosure of these documents in their entireties is hereby incorporated by reference in this application in order to more fully describe the state of the art to which this invention pertains.

The term "comprising" is intended herein to be open-ended, including not only the recited elements, but further encompassing any additional elements.

Various embodiments of the invention have been described broadly and generically herein. Each of the narrower species and subgeneric groupings falling within the generic disclosure also form the part of these inventions. This includes within the generic description of each of the inventions a proviso or negative limitation that will allow removing any subject matter from the genus, regardless or whether or not the material to be removed was specifically recited.

Although the invention has been described with reference to the examples provided above, it should be understood that various modifications can be made without departing from the invention.

The invention claimed is:

1. A method of selecting and amplifying polynucleotides on a solid support, comprising:
   a) providing a plurality of amplification oligonucleotides immobilized on a solid support comprising a planar surface or a population of beads;
   b) hybridizing a population of oligonucleotide probes to a subset of said amplification oligonucleotides, each of said oligonucleotide probes comprising a first portion which is complementary to the amplification oligonucleotides and a second portion which comprises a sequence identical to a selected region of a template polynucleotide;
   c) performing an extension reaction to extend hybridised amplification oligonucleotides to produce a population of support-bound capture oligonucleotides and a population of unextended amplification oligonucleotides, each capture oligonucleotide in said population comprising a sequence that is complementary to a selected region of a template polynucleotide;
   d) applying a population of template polynucleotides to the solid support under conditions such that the template polynucleotides selectively hybridise to the support-bound capture oligonucleotides, wherein a portion of the template polynucleotides comprises an adapter sequence identical to the unextended amplification oligonucleotides;
   e) extending the support-bound capture oligonucleotides that are hybridized to the template polynucleotides, thereby generating extension products, each of the extension products having a portion complementary to the template polynucleotides and a portion complementary to the unextended amplification oligonucleotides;
   f) amplifying the extension products, wherein the amplifying comprises annealing one or more of the unextended amplification oligonucleotides to one or more of the extension products and extending said one or more unextended amplification oligonucleotides, thereby producing a solid-phase amplification product; and g) sequencing a first strand of the solid-phase amplification product of step f) to obtain at least part of the nucleotide sequence of the template polynucleotide.

2. The method of claim 1, wherein said solid-phase amplification products comprise a binding site for a universal sequencing primer.

3. The method of claim 1 wherein the population of oligonucleotide probes comprises greater than $10^2$ different sequences.

4. The method of claim 1 wherein the population of oligonucleotide probes comprises greater than $10^3$ different sequences.

5. The method of claim 1 wherein the population of oligonucleotide probes comprises greater than $10^4$ different sequences.

6. The method of claim 1 wherein the population of oligonucleotide probes comprises greater than $10^6$ different sequences.

7. The method of claim 1 wherein the amplification is isothermal.

8. The method of claim 1, wherein the template polynucleotides in the nucleic acid sample comprise different sequences and the adapter sequence is the same for each of the template polynucleotides.

9. The method of claim 8, wherein the plurality of amplification oligonucleotides each comprise a common sequence that is identical to the adapter sequence that is the same for each of the template polynucleotides.

10. The method of claim 1, wherein the template polynucleotides comprise PCR amplicons.

11. The method of claim 1, wherein the template polynucleotides comprise genomic DNA fragments.

12. The method of claim 1, wherein the template polynucleotides are derived from cell-free DNA.

13. The method of claim 1, wherein the method further comprises the step of subjecting the extension products of step (e) to denaturation conditions prior to step (f).

14. The method of claim 1, wherein the method further comprises a wash step prior to step (f).

15. The method of claim 1, wherein each oligonucleotide probe further comprises a cleavage site between the first portion and the second portion.

16. The method of claim 15, wherein the cleavage site is a recognition site for a restriction endonuclease.

17. The method of claim 16, wherein the restriction endonuclease is a remote cutting restriction endonuclease.

* * * * *